US006900892B2

(12) United States Patent
Shchegrov et al.

(10) Patent No.: US 6,900,892 B2
(45) Date of Patent: May 31, 2005

(54) PARAMETRIC PROFILING USING OPTICAL SPECTROSCOPIC SYSTEMS

(75) Inventors: Andrei V. Shchegrov, Campbell, CA (US); Anatoly Fabrikant, Fremont, CA (US); Mehrdad Nikoonahad, Menlo Park, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 447 days.

(21) Appl. No.: 09/741,663

(22) Filed: Dec. 19, 2000

(65) Prior Publication Data

US 2002/0113966 A1 Aug. 22, 2002

(51) Int. Cl.$^7$ ................................................. G01J 4/00
(52) U.S. Cl. ...................... 356/369; 356/630; 356/636; 356/237.5; 250/559.22
(58) Field of Search ................................. 356/369, 630, 356/636, 237.1, 237.2, 237.5, 239.7; 250/559.22, 559.27, 225; 702/155, 166, 170

(56) References Cited

U.S. PATENT DOCUMENTS

| 5,751,427 A | 5/1998 | de Groot |
| 5,963,329 A | 10/1999 | Conrad et al. ............... 356/372 |
| 6,268,916 B1 | 7/2001 | Lee et al. |
| 6,657,736 B1 * | 12/2003 | Finarov et al. .............. 356/625 |

OTHER PUBLICATIONS

International Search Report for corresponding PCT application No. PCT/US01/49001 dated Apr. 18, 2002.
Patent Search conducted on Aug. 1, 2000.

"Ultraviolet–visible ellipsometry for process control during the etching of submicrometer features," N. Blayo et al., *J. Opt. Soc. Am. A.,* vol. 12, No. 3, Mar. 1995, pp. 591–599.
"Algorithm Implementation and Techniques for Providing More Reliable Overlay Measurements and Better Tracking of the Shallow Trench Isolation (STI) Process," D. Schramm et al., *SPIE: Conference on Metrology, Inspection, and Process Control of Microlithography XIII,*.Mar. 1999, pp. 116–122.

* cited by examiner

Primary Examiner—Frank G. Font
Assistant Examiner—Roy M. Punnoose
(74) Attorney, Agent, or Firm—Parson Hsue & de Runtz LLP

(57) ABSTRACT

A gallery of seed profiles is constructed and the initial parameter values associated with the profiles are selected using manufacturing process knowledge of semiconductor devices. Manufacturing process knowledge may also be used to select the best seed profile and the best set of initial parameter values as the starting point of an optimization process whereby data associated with parameter values of the profile predicted by a model is compared to measured data in order to arrive at values of the parameters. Film layers over or under the periodic structure may also be taken into account. Different radiation parameters such as the reflectivities $R_S$, $R_P$ and ellipsometric parameters may be used in measuring the diffracting structures and the associated films. Some of the radiation parameters may be more sensitive to a change in the parameter value of the profile or of the films then other radiation parameters. One or more radiation parameters that are more sensitive to such changes may be selected in the above-described optimization process to arrive at a more accurate measurement. The above-described techniques may be supplied to a track/stepper and etcher to control the lithographic and etching processes in order to compensate for any errors in the profile parameters.

92 Claims, 11 Drawing Sheets

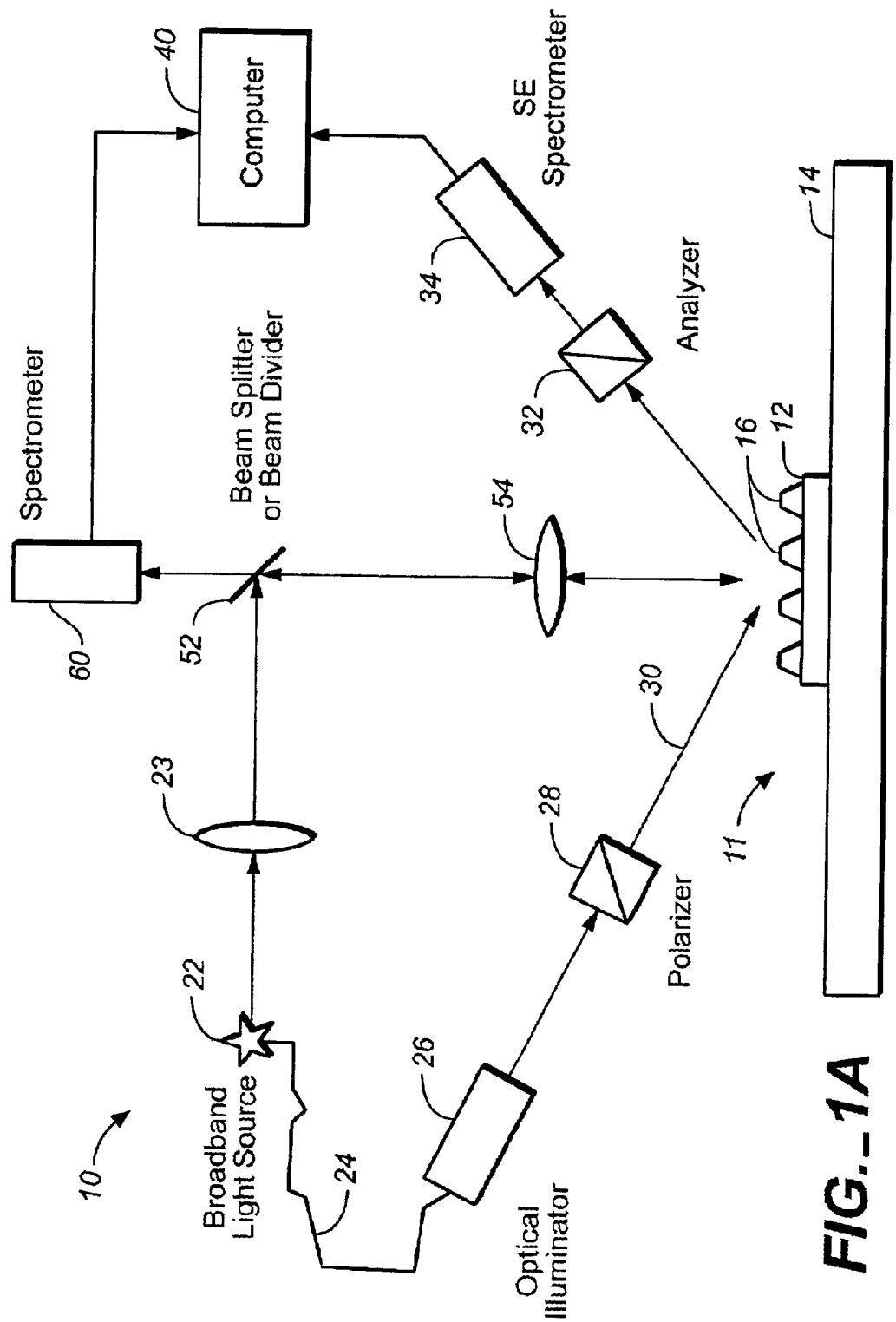
FIG._1A

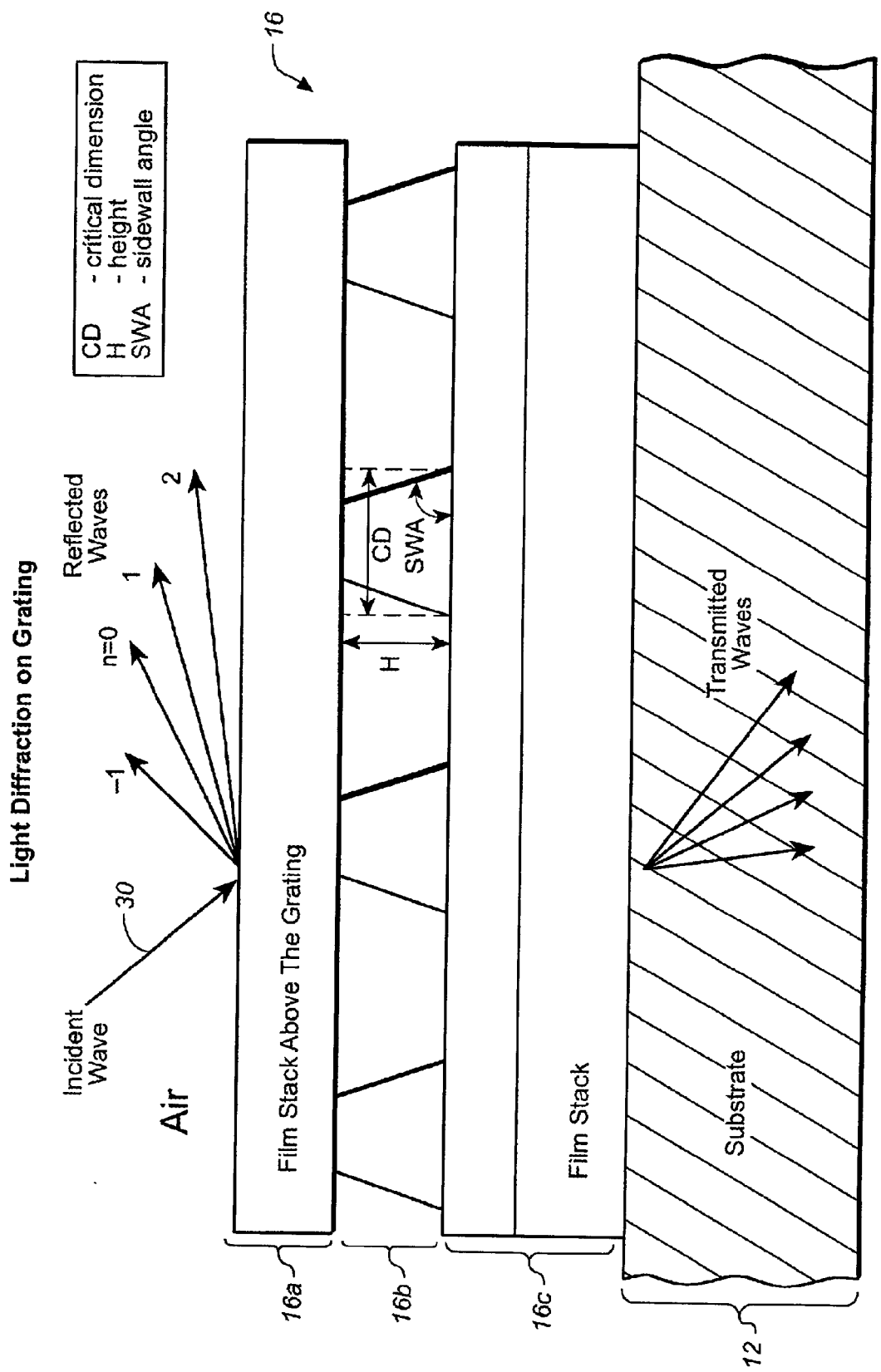
FIG._1B

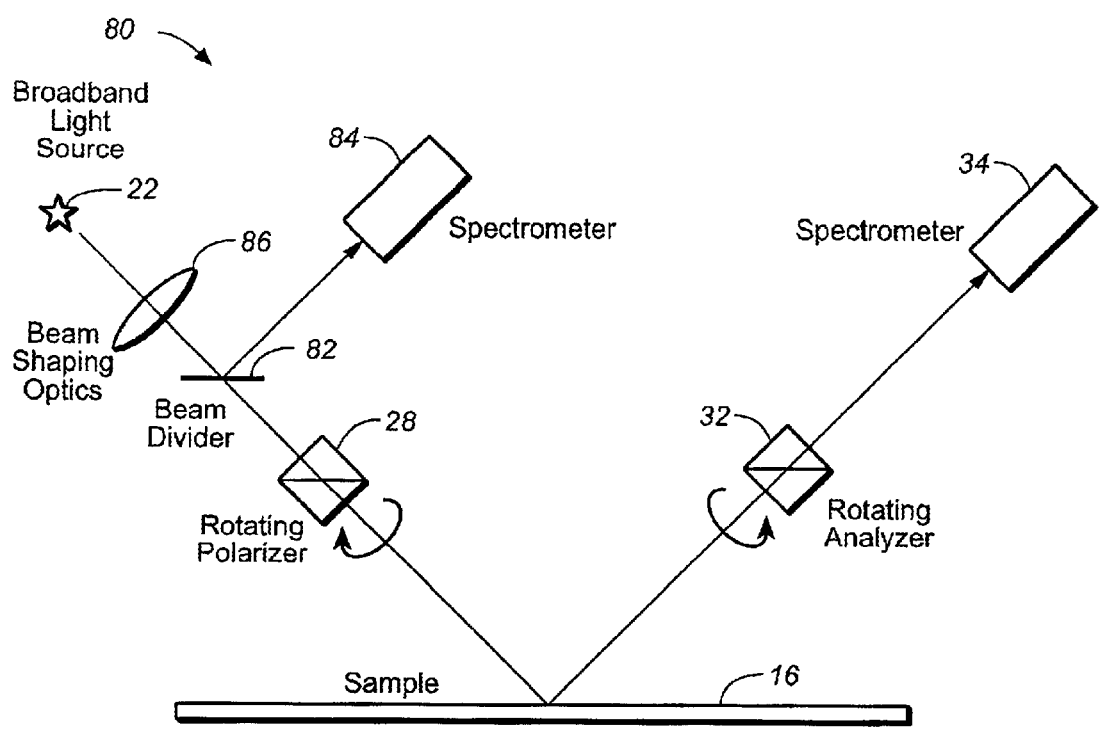
FIG._2

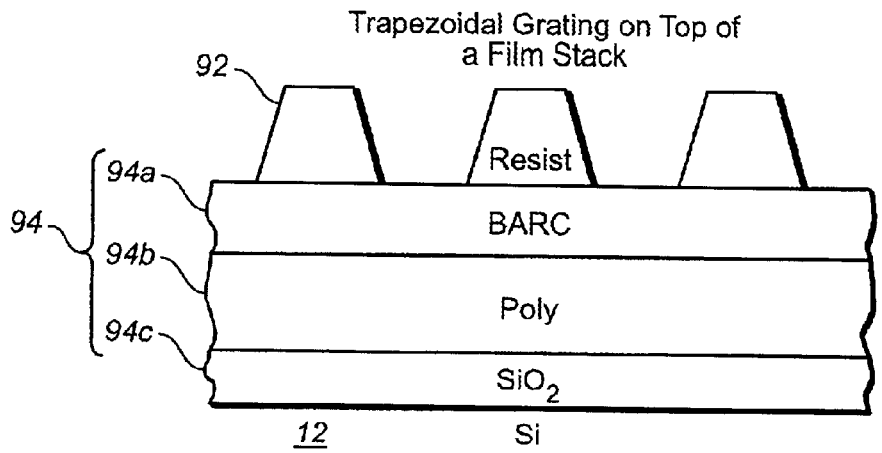
FIG._3A
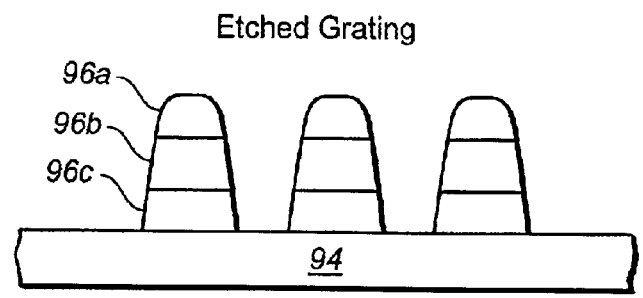
FIG._3B
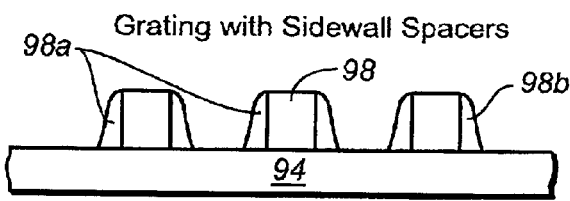
FIG._3C
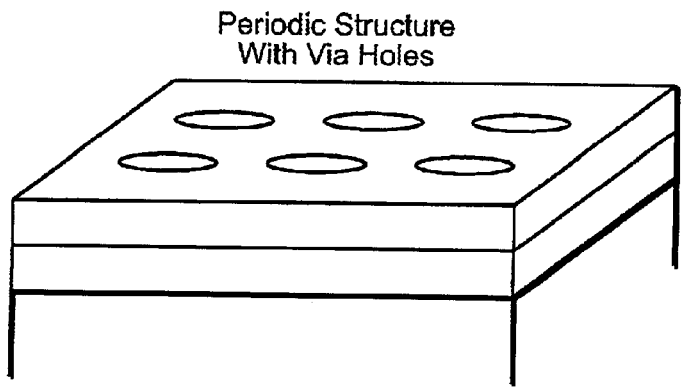
FIG._3D

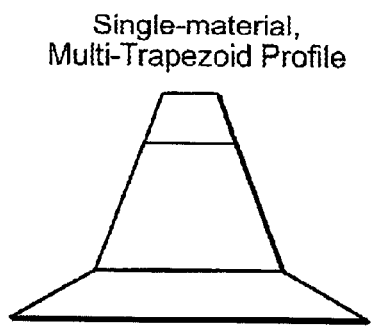
FIG._4A
Single-material, Multi-Trapezoid Profile
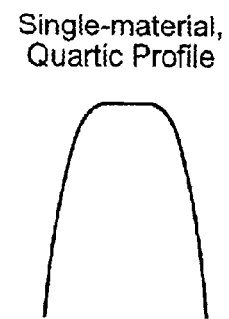
FIG._4B
Single-material, Quartic Profile
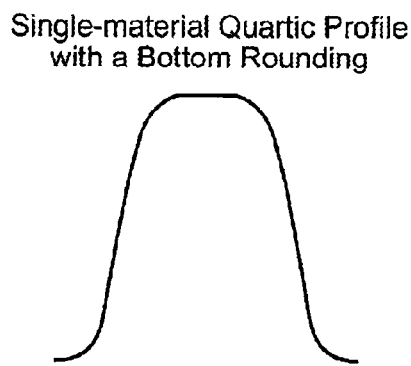
FIG._4C
Single-material Quartic Profile with a Bottom Rounding
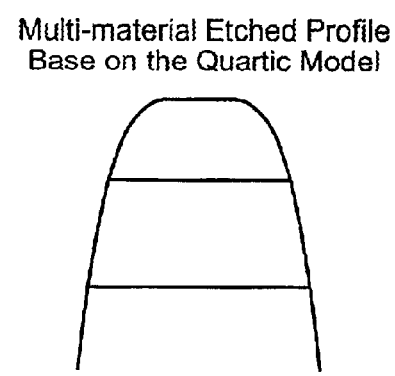
FIG._4D
Multi-material Etched Profile Base on the Quartic Model
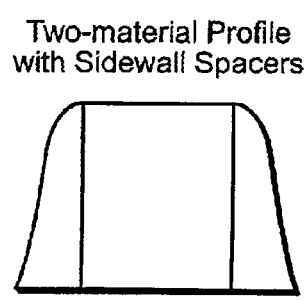
FIG._4E
Two-material Profile with Sidewall Spacers
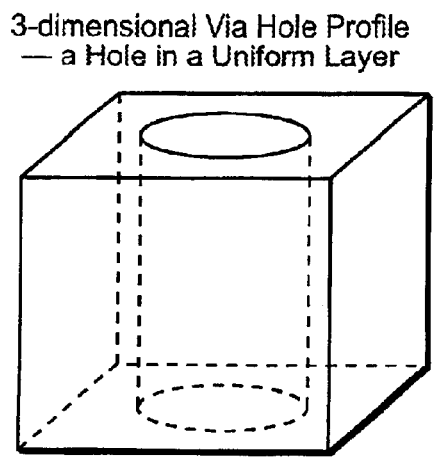
FIG._4F
3-dimensional Via Hole Profile — a Hole in a Uniform Layer

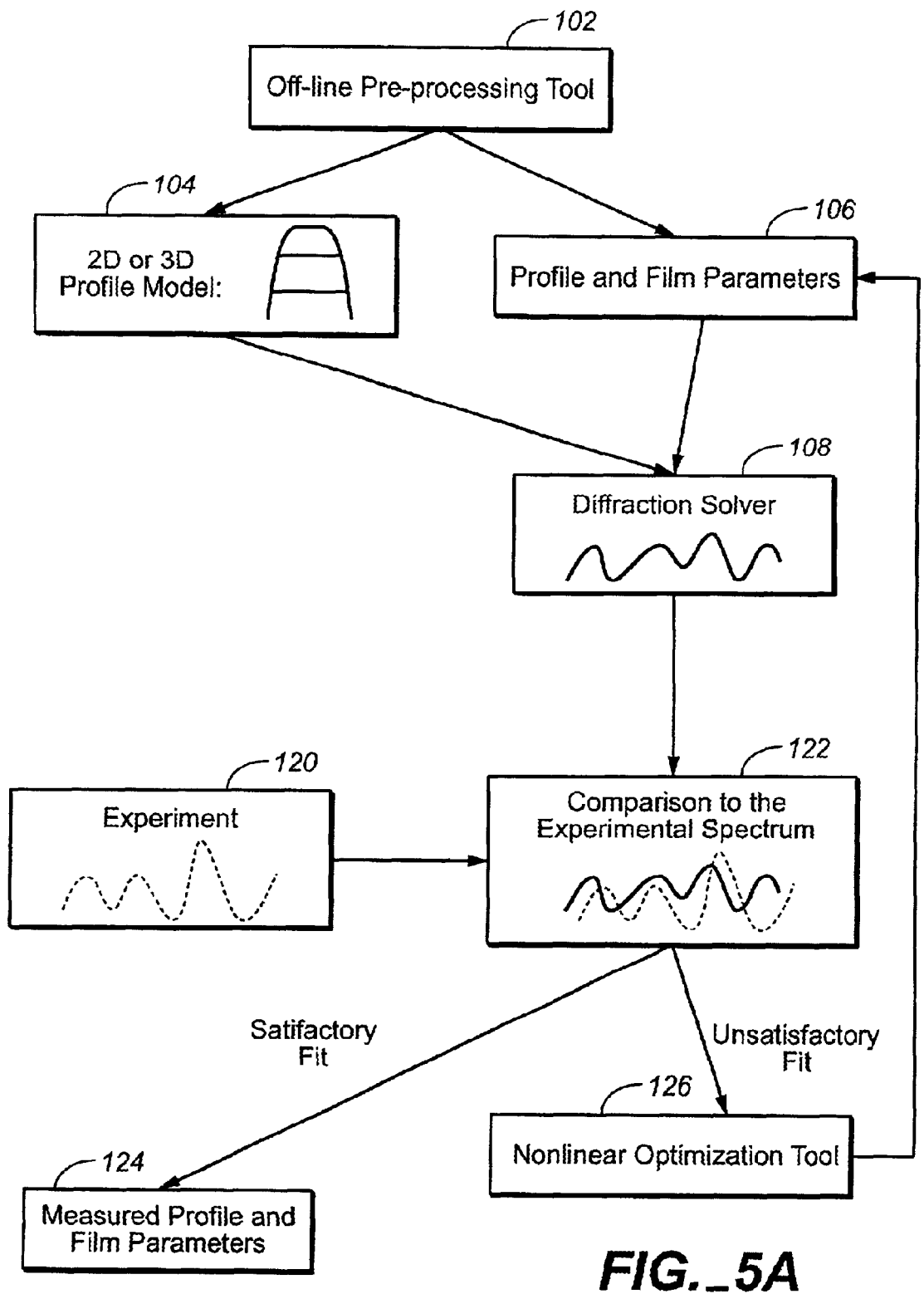
FIG._5A

Flowchart of Diffraction Solver
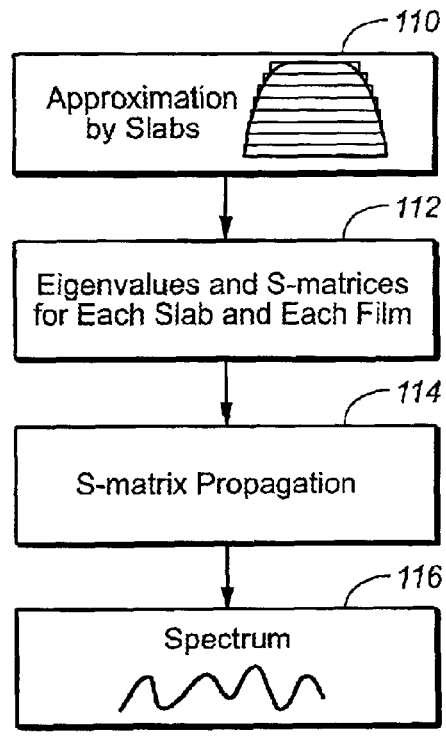
Selection of the Optimal Profile Model and Initial Seed
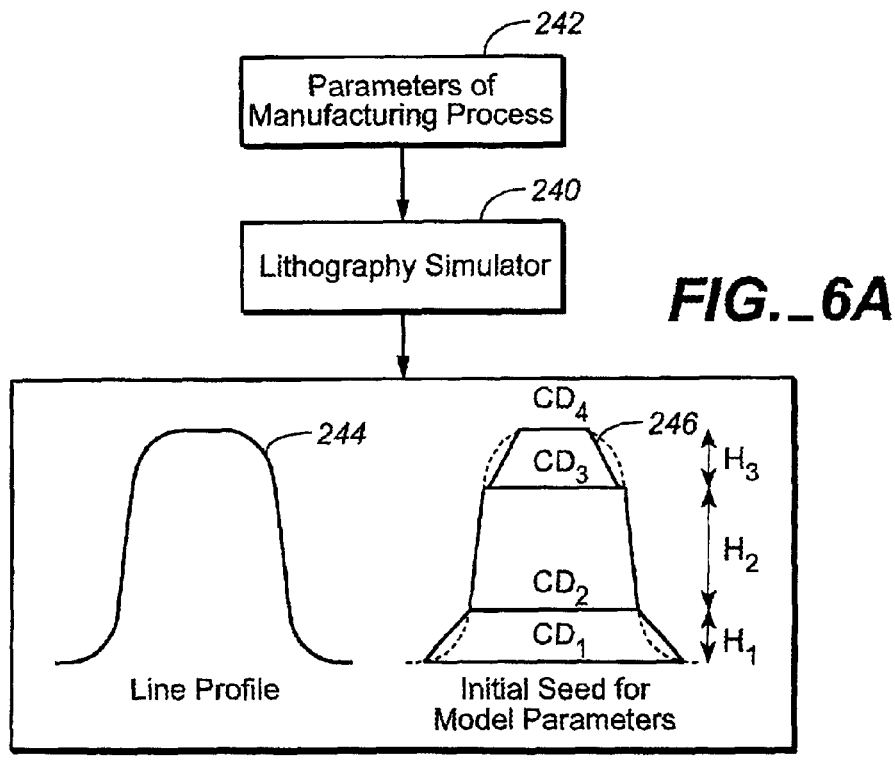
*FIG._5B*
*FIG._6A*

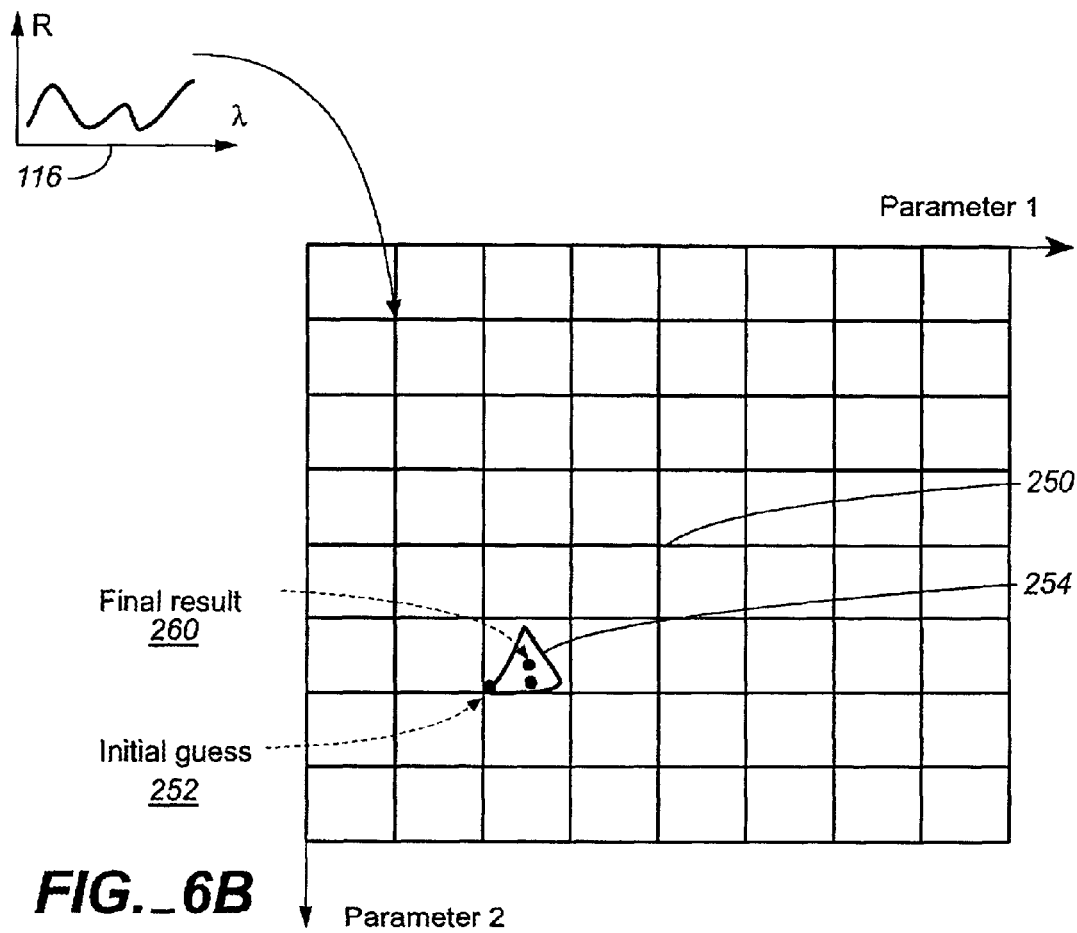
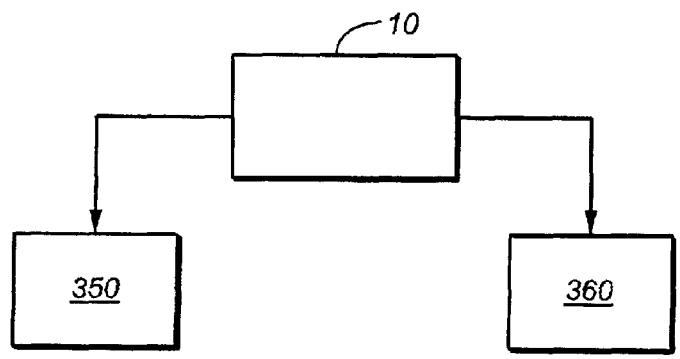

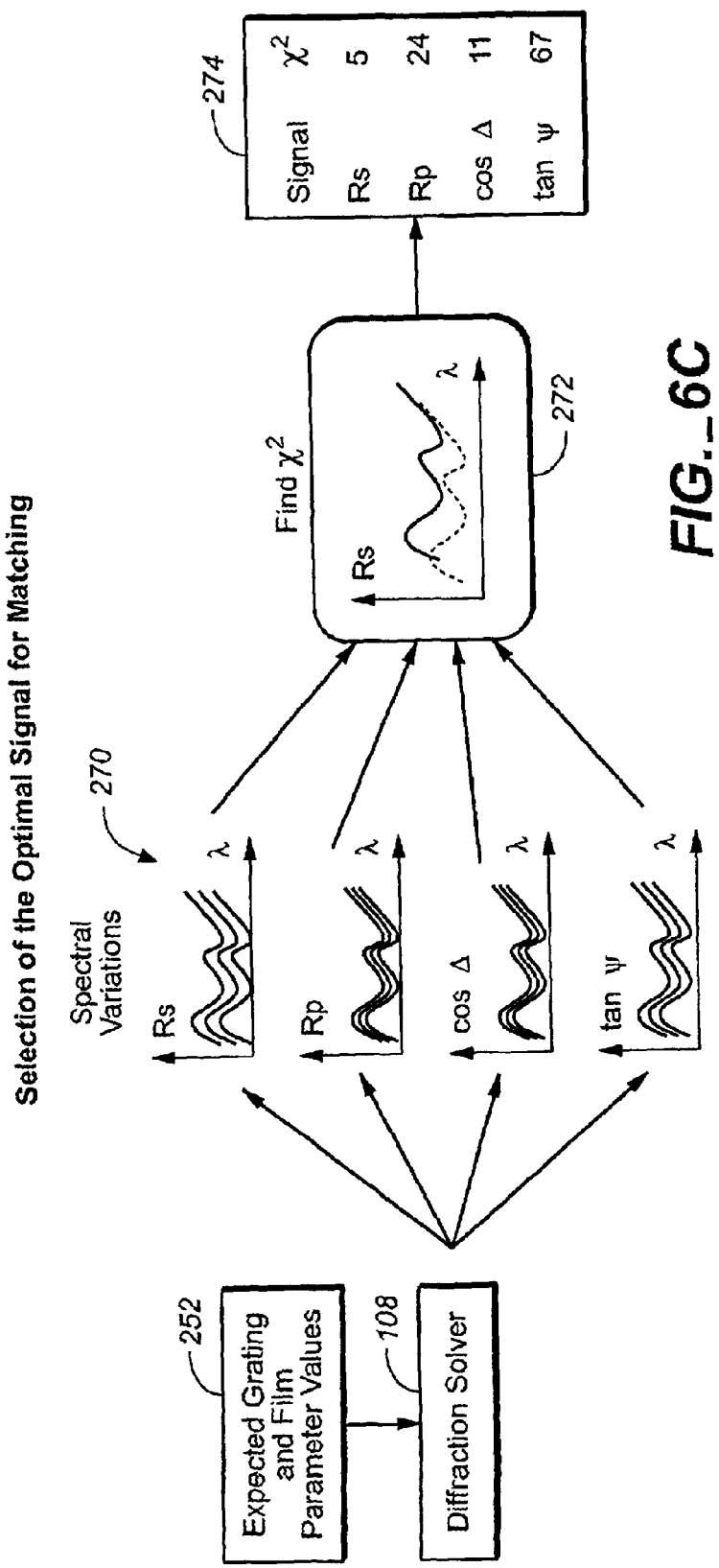
FIG._6C

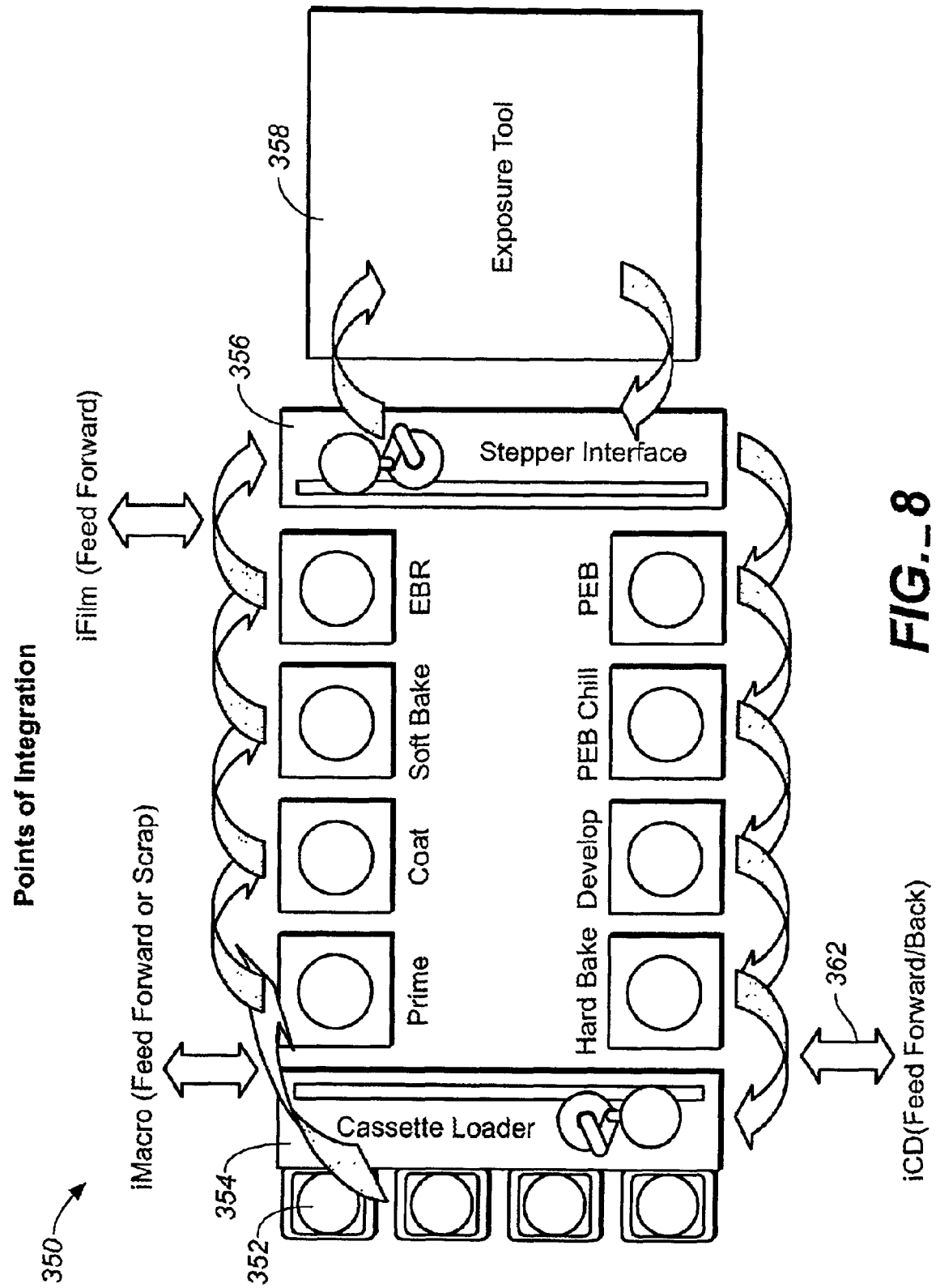
FIG._8

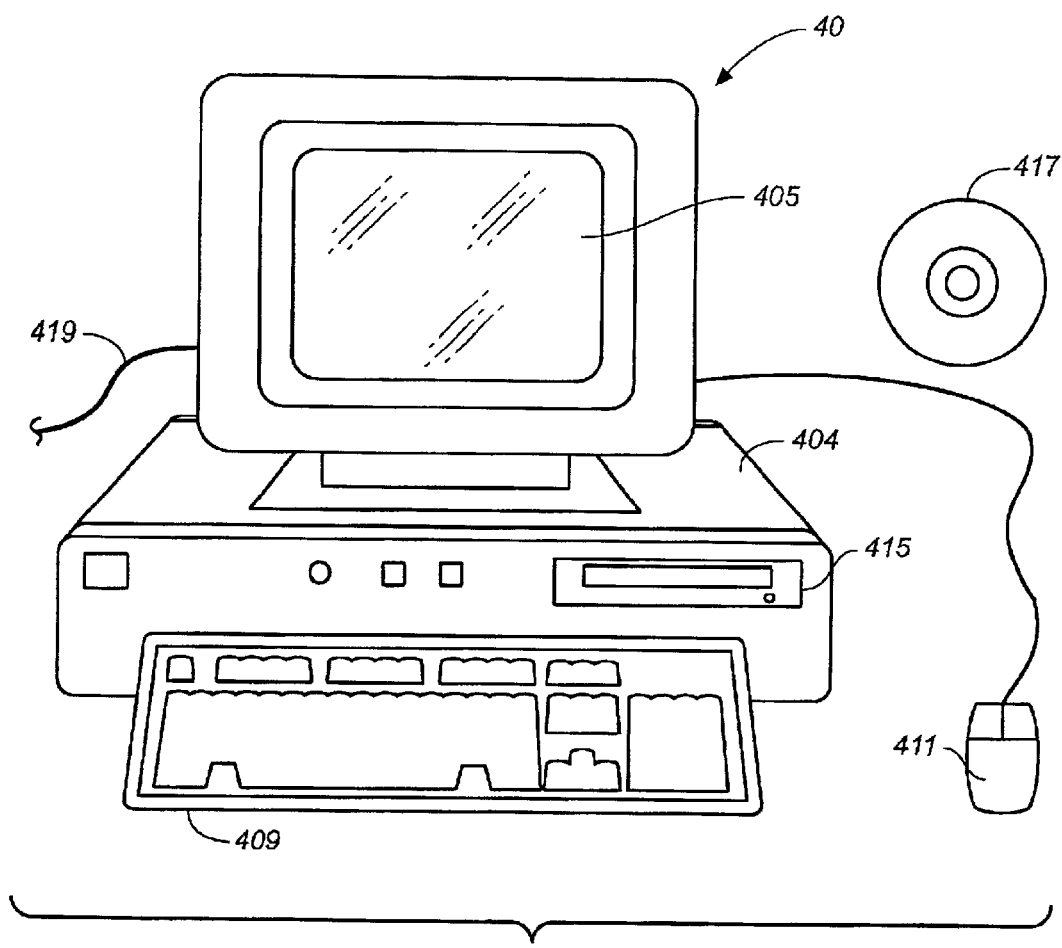
FIG._9

PARAMETRIC PROFILING USING OPTICAL SPECTROSCOPIC SYSTEMS

BACKGROUND OF THE INVENTION

This invention relates in general to systems for finding profiles of topographical features of small dimensions, such as those of a diffracting grating, and in particular to such systems using optical spectroscopic techniques.

As the integration density and speed of microelectronic devices increase, circuit structures continue to shrink in dimension size and to improve in terms of profile edge sharpness. The fabrication of state-of-the-art devices requires a considerable number of process steps. It is becoming increasingly important to have an accurate measurement of submicron linewidth and quantitative description of the profile of the etched structures on a pattern wafer at each process step. Furthermore, there is a growing need for wafer process monitoring and close-loop control such as focus-exposure control in photolithography.

Spectroscopic diffraction-based techniques are especially well suited for microelectronics metrology applications because they are nondestructive, sufficiently accurate, repeatable, rapid, simple and inexpensive relative to critical dimension-scanning electron microscopy. In such diffraction-based analysis techniques, typically a model of the profile is first constructed, where the model includes a number of parameters that can be varied. One or more diffraction intensity versus wavelength curves are calculated based on the model constructed and the curve(s) are compared with measured diffraction data from the sample. The parameters are then adjusted until a match is found between the curve(s) and the measured data.

The current methods being used include multi-slab models where a number of rectangular or trapezoidal slabs are put on top of one another to form a seed profile that is an approximation of the profile being measured. The parameters that can be adjusted include width and height of the rectangles or width, height and sidewall angle of the trapezoids. It is found that in the wafer processing processes, a number of very different profiles of structures may be encountered. The current methods are inadequate for measuring a wide variety of very different profiles in the manufacturing process. A simple increase of the number of slabs to model such variety of profiles requires the generation of huge libraries whose size grows exponentially with the number of slabs and the associated parameters. Furthermore, different sets of parameters, corresponding to different profiles, can produce indistinguishable spectroscopic data, resulting in a problem known as cross-correlation.

In U.S. Pat. No. 5,963,329, Conrad et al. proposed an improved method to measure actual profiles. In this model, the number of independent parameters or variables is reduced by adopting particular profile shapes such as a "S" line profile, by dividing the model line profile into two or more sub-profiles and providing a numerical model of each sub-profile so that fewer scaling factors may be used to adjust all slab widths and heights within the single sub-profile.

While the above-described method of Conrad et al. reduces the number of parameters that one needs to contend with, this method still has some drawbacks. Thus, it cannot be used for measuring line profiles made of more than material, and for measuring optical parameters as well as geometric parameters. It is therefore desirable to provide an improved model that can be used for determining the above mentioned samples in a manner so that the solution converges to a single solution without a high risk of cross-correlation.

As noted above, the shapes of line profiles encountered on semiconductor wafers during fabrication can take on a wide variety of shapes. Such line profiles are typically situated on and/or below layers of materials which may be the same as or different from the material of the profiles. When diffraction-based spectroscopic techniques are used to measure such profiles, the radiation used in the technique would interact with the one or more layers and transmitted or reflected radiation from the layers is detected by the detectors that are used for detecting radiation from the line profile. Where it is not possible or very difficult to separate the contribution of the signal due to the layers from the contribution of the signal due to the line profile, it is desirable for any technique used to measure the parameters of such layers simultaneously with measurement of the line profile. None of the existing techniques has such capability. It is therefore desirable to provide an improved system where the contribution of such layers to the detector signal can be taken into account.

SUMMARY OF THE INVENTION

Semiconductor devices are fabricated by processing equipment with certain set parameters of the manufacturing process, such as the time, temperature, focus and exposure dose in the lithography and other parameters, such as the time and temperature for the deposition of certain layers, or the time, and nature of etching processes. Once these parameters are known, it is possible to simulate the profile of the structures that will result from such manufacturing process. A gallery of seed profiles or profile types may be used as possible starting points for finding the actual shapes of line profiles. Preferably, knowledge of manufacturing process parameters may be utilized in the construction of a gallery of profile types from which a particular profile type can be chosen for matching with the measured data. Also preferably, knowledge of manufacturing process parameters is utilized to select from the gallery a particular profile type that would serve as the best seed profile for the purpose of finding the actual profile of structures.

As noted above, the diffracting structure to be measured is frequently located on and/or below one or more layers of the same or different material, so that the detector employed would detect radiation influenced by such layers as well as diffraction from the diffracting structure. These layers would have to be taken into account in the model. Parameters such as thickness and index of refraction (n and k) of these layers would be more sensitive to certain measurement parameters than others. This is also true of the parameters characterizing the diffracting structure. Therefore, in another embodiment of the invention, more than one set of radiation data may be generated from each profile type, where the sets of radiation data generated are of different radiation parameters, such as reflectance or transmittance parameters and ellipsometric parameters. For a given change in the parameter of the profile type (e.g., width, height, sidewall angle, index of refraction of the diffracting structure and thickness and index of refraction of the one or more layers) may be more sensitive to the ellipsometric parameters than to the transmittance or reflectance parameters, or vice versa. In such event, it may be desirable to choose the set of radiation data and the associated radiation parameters that are more sensitive to a change in the parameter of the profile or a characteristic of the one or more layers to improve the accuracy and precision of the modeling and matching algorithm. This feature can also be used where the effects of the layers need not be taken into account, such as where the effects are known, can be ignored or where there is no layer associated with the structure.

Independent of the above considerations, reflectance or transmittance parameters and ellipsometric parameters of the collected radiation may be used together for deriving one or more parameters of a profile with arbitrary shape.

The gallery of profile types may be stored in a database made available to users and an optional processor may be used to select the profile type from the gallery and compare the detected measured data to that associated with the selected profile type to arrive at a set of values of the one or more parameters of the profile type.

Where the profiles measured are useful for controlling a wafer manufacturing process, the measured information may be used to control the processing system for adjusting one or more processing parameters. Thus, if the profile of the structure measured indicates a problem in the processing system, the processing system may be adjusted to reduce or eliminate the effects of the problem. Any one of the above-described techniques may be used to find a profile of a structure and/or characteristics of one or more layers in the vicinity of the structure, and these values may then be supplied to a semiconductor wafer processing machine, such as a track, stepper and/or etcher, to control the lithographic and/or etching process in order to compensate for any errors in one or more parameters of the profile that has been discovered. The track, stepper and/or etcher may form a single tool with a system for finding the one or more parameters of a profile, or may be instruments separate from it.

While the above-described features may be implemented as a stand-alone system and integrated with optical equipment for carrying out the measurements, it is possible for existing optical measurement equipment to be modified or otherwise enabled so that it has the capability described above. Thus, the above-described features may be embodied as a program of instructions executable by computer to perform the above-described different aspects of the invention. Hence any of the techniques described above may be performed by means of software components loaded into a computer or any other information appliance or digital device. When so enabled, the computer, appliance or device may then perform the above-described techniques to assist the finding of value(s) of the one or more parameters using measured data from a diffracting structure and/or the associated one or more layers. The software component may be loaded from a fixed media or accessed through a communication medium such as the internet or any other type of computer network.

Each of the inventive features described above may be used individually or in combination in different arrangements. All such combinations and variations are within the scope of the invention.

BRIEF DESCRIPTION OF THE DRAWINGS

FIG. 1A is a schematic view of a spectroscopic measurement device useful for illustrating the invention.

FIG. 1B is a cross-sectional view of a two-dimensional grating and associated layers useful for illustrating the invention.

FIG. 2 is a schematic view of another spectroscopic measurement device useful for illustrating the invention.

FIGS. 3A, 3B, 3C are cross-sectional views of two-dimensional structures encountered in semiconductor manufacturing useful for illustrating the invention.

FIG. 3D is a perspective view of a three dimensional periodic structure with via holes useful for illustrating the invention.

FIGS. 4A–4F are sample profiles to illustrate a gallery of profile types or models to illustrate an embodiment of the invention.

FIG. 5A is a flow chart of profile and film measurement to illustrate an embodiment of the invention.

FIG. 5B is a flow chart illustrating in more detail the diffraction solver in the flow chart of FIG. 5A.

FIG. 6A is a flow chart illustrating the selection of the optimum profile type or model and the value of parameters for the initial seat values.

FIG. 6B is a flow chart illustrating the process for selecting the optimal radiation parameter and the corresponding set of radiation data for matching with measured data to illustrate one aspect of the invention.

FIG. 6C is a schematic diagram illustrating the selection of the starting point for nonlinear optimization from a course library to illustrate an aspect of the invention.

FIG. 7 is a schematic block diagram illustrating a wafer processing apparatus including a track/stepper and an etcher and a spectroscopic measurement device where information from a diffracting structure and/or associated structures from the device as used to control the manufacturing process and the track, stepper and/or etcher to illustrate the invention.

FIG. 8 is a schematic block diagram illustrating in more detail the track/stepper of FIG. 7.

FIG. 9 is a block diagram showing a representative sample logic device in which aspects of the present invention may be embodied.

For simplicity and description, identical components are labeled by the same numerals in this application.

DETAILED DESCRIPTION OF THE EMBODIMENTS

Even though much of the description below of algorithms and methods are described in terms of the reflected or transmitted intensities of the diffraction caused by the diffracting structure, it will be understood that the same techniques and algorithms may be used for data containing information concerning changes in the polarization state over different wavelengths (e.g. ellipsometric parameters $\Delta$ and $\Psi$ as functions of wavelength). For this reason, it may be advantageous to employ an instrument which is capable of measuring both the reflected or transmitted intensities of the diffraction caused by the structure as well as changes in polarization state caused by the diffraction of the structure. A suitable system is described below in reference to FIG. 1A.

FIG. 1A is a schematic view of a spectroscopic diffraction-based metrology system to illustrate the preferred embodiment of the invention. As shown in FIG. 1A, system 10 may be used to measure reflected or transmitted intensities or changes in polarization states of the diffraction. As shown in FIG. 1A, a semiconductor wafer 11 may comprise a silicon substrate 12, and a structure 16 thereon that may include a photoresist pattern on and/or over film stack(s), where the film(s) are at least partially light-transmissive and has a certain film thickness and refractive index (n and k, the real and imaginary components of the index).

An XYZ stage 14 is used for moving the wafer in the horizontal XY directions. Stage 14 may also be used to adjust the z height of the wafer 11. A polychromatic or broadband radiation source such as white light source 22 supplies light through a fiber optic cable 24 which randomizes the polarization and creates a uniform light source for illuminating the wafer. Preferably, source 22 supplies electromagnetic radiation having wavelengths in the range of at least 180 to 800 nm. Upon emerging from fiber 24, the radiation passes through an optical illuminator 26 that may include an aperture and a focusing lens or mirror (not shown). The aperture causes the emerging light beam to illuminate an area of structure 16. The light emerging from illuminator 26 is polarized by a polarizer 28 to produce a polarized sampling beam 30 illuminating the structure 16.

The radiation originating from sampling beam 30 is reflected by structure 16, passed through an analyzer 32 and to a spectrometer 34 to detect different spectral components of the reflected radiation, such as those in the spectrum of the radiation source 22, to obtain a signature of the structure. In one mode (spectrophotometry mode) of operation, the reflected intensities are then used in a manner described below to find the value(s) of one or more parameters of structure 16. The system 10 can also be modified by placing the spectrometer 34 on the side of structure 16 opposite to illumination beam 30 to measure the intensities of radiation transmitted through structure 16 instead for the same purpose. These reflected or transmitted intensity components are supplied to computer 40.

Alternatively, the light reflected by the structure 16 is collected by lens 54, and passes through the beam splitter 52 to a spectrometer 60. The spectral components at different wavelengths measured are detected and signals representing such components are supplied to computer 40. The light reflected by structure 16 may be supplied by source 22 through illuminator 26 as described above or through other optical components in another arrangement. Thus, in such arrangement, lens 23 collects and directs radiation from source 22 to a beam splitter 52, which reflects part of the incoming beam towards the focus lens 54 which focuses the radiation to structure 16. The light reflected by the structure 16 is collected by lens 54, passes through the beam splitter 52 to spectrometer 60.

When the system 10 is operated in another mode (spectroscopic ellipsometry mode) used to measure the changes in polarization state caused by the diffraction by the structure, either the polarizer 28 or the analyzer 32 is rotated (to cause relative rotational motion between the polarizer and the analyzer) when spectrometer 34 is detecting the diffracted radiation from structure 16 at a plurality of wavelengths, such as those in the spectrum of the radiation source 22, where the rotation is controlled (not shown) by computer 40 in a manner known to those skilled in the art. The diffracted intensities at different wavelengths detected are supplied to computer 40, which derives the changes in polarization state data at different wavelengths from the intensities in a manner known to those in the art. See for example U.S. Pat. No. 5,608,526, which is incorporated herein by reference.

FIG. 1B is a cross-sectional view of the structure 16 on substrate 12, which structure comprises a diffracting structure 16b situated between the film stack 16a above the structure and the film stack 16c underneath the structure and an incident electromagnetic beam 30 to illustrate the invention. Thus, the incident beam 30 of the electromagnetic radiation first encounters the interface between the air and the film stack 16a and interfaces that may be present within the stack. Next, the portion of the radiation from beam 30 that penetrates the film stack 16a is diffracted by the grating structure 16b. At least some of the radiation from beam 30 will reach the film stack 16c underneath the grating and be reflected by or transmitted through interfaces associated with stack 16c. The total light reflectance is affected both by the grating and by the film stacks above and/or below the grating. Multi-layer interference, caused by multiple reflections between the films and the grating, creates a complicated pattern in a reflectance spectrum, which can be used for measuring parameters of the structure. A part of radiation from beam 30 that is not reflected or diffracted as described above will be transmitted into the substrate 12. As shown in FIG. 1B, the grating 16b has a height of H, a critical dimension ("CD") and a sidewall angle (SWA) as indicated.

FIG. 2 is a schematic view of an alternative spectroscopic measurement system 80 to illustrate the invention. The system of FIG. 2 differs from that in FIG. 1A in that it uses the same optical components for both the spectrophotometry mode measurement as well as the ellipsometry measurement, and thus has fewer optical components. On the other hand, the two modes need to be employed sequentially and not simultaneously as is possible with the apparatus of FIG. 1A. As before, where there is relative rotational motion between the polarizer 28 and analyzer 32 when a measurement is taken, the system 80 of FIG. 2 operates as an ellipsometer. This can be achieved by rotating either the polarizer 28 or the analyzer 32, or both. Where there is no relative rotation between polarizer 28 and analyzer 32 (such as where both did not rotate, or rotate at the same speed), instrument 80 operates as a spectrophotometer or reflectometer.

As shown in FIG. 2, system 80 further includes a beam divider 82 which diverts the portion of the illumination beam from source 22 to a spectrometer 84 which measures variations in the intensity of the illumination beam so that the effects of such variations may be removed from the measurements. Beam shaping optics 86 is employed to shape the illumination beam, such as by collimating or focusing the beam.

While some diffracting structures may take on simple geometric shapes such as that illustrated in FIG. 1B, in some instances, these structures can take on more complex shapes. When this is the case, it is desirable to provide a model by which a much wider variety of profiles of structures can be predicted than can conventional models. FIGS. 3A–3D illustrate the type of structures that may be encountered during the wafer manufacturing process. FIG. 3A is a cross-sectional view of a line grating on top of a film stack, where the cross-section of each line is in the shape of a trapezoid 92, and the film stack comprises layers 94a (bottom anti-reflection coating, or BARC), 94b (polysilicon), 94c (silicon dioxide) on top of a substrate 12.

Alternatively, the structure may comprise periodic lines where each line comprises a stack of several different materials, where the cross-sectional shape of the lines is curved. As illustrated in FIG. 3B, the diffracting structure comprises three layers: 96a, 96b, 96c and the diffracting structure is located on top of a film 94 which may comprise one or more layers. The structure in FIG. 3B typically results from the process of shallow trench isolation ("STI"). Yet another example of a realistic structure encountered in wafer manufacturing is illustrated in FIG. 3C which comprises a line grating with sidewall spacers, made of a material different form that of the line grating. As shown in FIG. 3C, each line grating comprises a center portion 98a which is substantially rectangular in cross-section and two sidewalls 98a, 98b on the two sides of the rectangle where the line structures are situated on top of a film 94. The sidewall spacers of FIG. 3C are typically used to control the desired shape of polysilicon lines 98 in the process of reactive ion etching ("RIE").

FIG. 3D is a perspective view of a periodic structure with via holes where the holes may penetrate one or more layers. The via holes provide vertical connections from one metallization layer to another. Thus, the structure 16 of FIGS. 1A, 2 may include one or more of the diffracting structures and layers shown in FIGS. 1B, 3A–3D. From the shapes of the structures illustrated in FIGS. 3A–3D, it will be evident that prior art methods, such as the one described in U.S. Pat. No. 5,963,329, may be inadequate for measuring the more complex structures illustrated in such figures.

FIGS. 4A–4F illustrate examples of profile models which may advantageously serve as the seed profiles or profile types that may be employed to derive the actual profile of a diffraction structure encountered in semiconductor manufacturing. FIG. 4A illustrates a cross-sectional view of a profile type comprising a single-material, multi-trapezoid profile, characterized by values of CD, height and sidewall angle for each trapezoid. When the sidewall angles are fixed at 90 degrees, this profile type becomes a multi-slab model. The bottom trapezoid models a footer.

FIG. 4B is a cross-sectional view of a single-material, quartic profile which may be represented by the polynomial expression $y=ax^4$, characterized by the height of the profile and coefficient value a. FIG. 4C is a cross-sectional view of a single-material, quartic profile with a bottom rounding (i.e., rounded footer), characterized by height, quartic coefficient a and parameters of the bottom rounding or footer. More than one model may be used for the footer, one example being a model using a smooth function (e.g. straight line as shown in FIG. 4A, or curved line such as that of a quadratic function). FIG. 4D is a cross-sectional view of a multi-material, etched quartic profile of the form $y=ax^4$, characterized by coefficient a and the thicknesses of each of the three layers. FIG. 4E is a cross-sectional view of a two-material profile with sidewall spacers, characterized by height, edge and profiling parameters for the inner and outer materials of the spacers, such as common height value for the inner and outer materials, different CD values for the inner and outer materials, and a sidewall angle for the outer material. FIG. 4F is a perspective view of a three-dimensional structure with the via hole profile in a uniform layer, characterized by the height and hole parameters (radius for a circular hole).

While the quartic profile is illustrated in FIGS. 4B, 4C and 4D, profiles that can be described using other polynomial expressions may also be used and are within the scope of the invention, such as quadratic parabolas, or a combination of quartic and quadratic parabolas. In the same vein, while the profile type in FIG. 4A includes multiple slabs that are trapezoidal, slabs defined by one or more analytical functions, such as where one side of the trapezoid is curved, may be employed and are within the scope of the invention.

The profile types in FIGS. 4A–4F do not include layers of material which may lie above and/or below the actual diffracting structures measured. These layers can also be modeled as described below using parameters for such layers, such as thicknesses and indices of refraction (referred to herein also as film parameters), so that the models constructed using the profile types can take into account the layers above and/or below the diffracting structures measured. In addition, the profile types themselves may include layers, such as those illustrated in FIG. 4D. The layers of the profile type in FIG. 4A can be modeled using not only geometric parameters, such as the coefficient a and height of each of the three layers, but also the complex index of refraction of each of the materials in the three layers of the profile itself.

Before any measurement of structure 16 is made using the apparatuses in FIGS. 1A and 2, a gallery of profile types such as those illustrated in FIGS. 4A–4F is first prepared and stored in the database. FIG. 5A is a flowchart of profile and film measurement to illustrate a process using a model to measure the parameters of the diffracting structure. Where the structure is situated on and/or below one or more layers of materials, the model may also be used to measure one or more parameters of such layers. As shown in FIG. 5A, an off-line pre-processing tool 102 is used to provide the gallery described above together with the seed profile and film parameters associated with each of the profile types, such as the profile types illustrated in FIGS. 4A–4F, together with layers over and below the profiles shown. The profile parameters can include, for example, CD, height, sidewall angle, parameters associated with polynomial expressions such as the coefficient a and height of quartic profiles, parameters of the bottom rounding and of the spacers, and the indices of refraction (n and k) parameters of materials of the line profile. The film parameters may include thicknesses of the layers and the indices of refraction (n and k).

Tool 102 then computes from the profile types and their associated profile and film parameters, as well as initial values of such parameters (e.g. based on estimation, or the knowledge or simulation of the fabrication process), predicted spectra radiation data associated therewith in a diffraction solver 108. The operation of the diffraction solver 108 is illustrated in more detail in FIG. 5B. As shown in FIG. 5B, the profile type may be approximated by slabs (block 110). Eignvalues and S-matrices for each slab and each film underneath and/or over the profile type are computed (block 112). S-matrices are then propagated (block 114) to arrive at a spectrum (block 116), which is the predicted radiation data when a profile is measured using the instruments of FIGS. 1A, 2. For a detailed description of the modeling process applied by solver 108, please see the references below:

M. G. Moharam, E. B. Grann, D. A. Pommet, and T. K. Gaylord, "Formulation of stable and efficient implementation of the rigorous coupled-wave analysis of binary gratings," J. Opt. Soc. Am. A, vol. 12, pp. 1068–1076 (1995);

L. Li, "Formulation and comparison of two recursive matrix algorithms for modeling layered diffraction gratings," J. Opt. Soc. Am. A, vol. 13, pp. 1024–1035 (1996); and M. G. Moharam, "Coupled-wave analysis of Two-Dimensional Dielectric Gratings," PROC. SPIE, vol. 883, pp. 8–11 (1988).

Returning now to FIG. 5A, the spectra associated with the actual diffracting structure and the film(s) in structure 16 are then measured using the apparatus of either FIG. 1A or FIG. 2 (block 120) or any other suitable apparatus and the measured data is then compared with the predicted spectrum from the diffraction solver 108 (block 122). If there is a good match between the two spectra, the initial values of the parameters of the profile type and of the film(s) then correctly predict those of the actual structure and film(s) that are measured (block 124). If the match is less than satisfactory (block 126), the profile and film parameters (block 106) are then varied or adjusted by means of a nonlinear optimization tool (block 126) in a feed back path. The steps of the diffraction solver 108 and the comparison 122 are repeated until there is a satisfactory match between the predicted spectrum and the experimental spectrum. Any number of nonlinear optimization tools may be employed, such as those described in the following articles:

J. Nocedal and S. J. Wright, "Numerical Optimization," Springer-Verlag, New York, N.Y. (1999); and D. T. Pham and D. Karaboga, "Intelligent Optimization Techniques: Genetic Algorithms, Tabu Search, Simulated Annealing and Neural Networks," Springer-Verlag, New York, N.Y. (2000).

As described above in reference to FIGS. 3A–3D, the actual diffracting structures encountered in wafer processing include a wide variety of different shapes. According to one aspect of the invention, information concerning the manufacturing process may be advantageously used in selecting profile types for the gallery which serve as the seed profiles for the modeling process. Thus, the gallery of FIGS. 4A–4F are selected keeping in mind the structures encountered in semiconductor manufacturing, such as those in FIGS. 3A–3D.

As noted above, semiconductor devices are fabricated by processing equipment with certain set parameters of the manufacturing process, such as the time, temperature, focus and exposure dose in the lithography and other parameters for deposition of certain layers or of etching processes. Once these parameters are known, it is possible to derive the profile of the structures that will result from such manufacturing process. A software tool that may be used to simulate the profile of the structures resulting from the manufacturing process is PROLITH™ simulator software, available from KLA-Tencor Corporation, the assignee of the present application, in San Jose, Calif. This software is described in *Inside PROLITH*, by Chris A. Mack, Finle Technologies (Austin, Tex.: 1997). Another possible tool that may be used to simulate the profile of the structures resulting from the manufacturing process is Solid_C, from Sigma_C, Munich, Germany. Thus, once information concerning the manufacturing process, such as the values of the manufacturing process parameters (e.g., time, temperature) is available, the profile that is predicted from such parameters may then be used to select a profile type from the gallery of profile types to serve as the seed profile for the modeling process illustrated in FIGS. 5A, 5B. In addition, the predicted profile arrived at using manufacturing process information may also be used to select a set of initial values of the parameters associated with the profile type, such as initial values of CD, sidewall angle, height, coefficient a and height of quadric expressions or coefficients of other polynomial-type expressions, and a process window in which these parameters are expected to vary. This process is illustrated in FIG. 6A.

As illustrated in FIG. 6A, a lithography simulator 240 (e.g. PROLITH™ simulator) simulates, from parameters of manufacturing process 242, a line profile 244. From the simulated line profile 244, the profile type of FIG. 4A in the gallery that is the closest match to line profile 244 is then selected as the seed profile. The line profile 244 is also used to select initial values of the different parameters of such profile type, so that the predicted profile using such profile type is the closest match to simulated profile 244. Thus, in the example in FIG. 6A, initial values of the seven parameters $CD_1$, $CD_2$, $CD_3$, $CD_4$ and $H_1$, $H_2$, $H_3$ are selected for the modeling process of FIGS. 5A, 5B so that the predicted profile 246 shown in FIG. 6A is the closest match to simulated profile 244. By making use of the manufacturing process as described above, a profile type with initial parameter values that is close to the actual structure being measured is selected as the seed profile for the modeling process, so that the non-linear optimization process illustrated in FIG. 5A can converge rapidly.

The above-described modeling process starting with the seed profile or profile type and with the initial parameter values is illustrated in FIG. 6B. As noted above, from information available from the manufacturing process, it is possible to ascertain a process window in which parameter values may vary. Such window is illustrated in FIG. 6B, where the ranges of the parameters 1 and 2 shown are the ones through which these two parameters may vary. The window may be defined with respect to a center point 250, and an amount that each parameter is allowed to deviate from the value at this center point; the center point and the deviation allowed for each parameter are derived from the manufacturing information. The process window may be divided into different sections by a set of vertical lines and a set of horizontal lines, where the intersections between the two sets of lines form a set of points, each of which correspond to a pair of values for the two parameters. Solver 108 may be used to derive the radiation spectra corresponding to these pairs of values, where the spectra and their corresponding pairs form a coarse library. Where the profile type is characterized by more than two parameters, the window would be a space with more than two variables, and each intersection point would correspond to a set of more than two parameters.

After this coarse library has been constructed, the spectra in the library are matched with the simulated data to find the closest match. The intersection point 252 corresponding to the closest matching spectrum indicates the set of initial parameter values that is a good starting point to perform the optimization process of FIG. 5A. The line 254 in FIG. 6B illustrates schematically the path taken by the optimization process, arriving at the final result at point 260 in FIG. 6B.

In the profile type of FIG. 4A, for example, there will be at least three parameter values: CD, height ("H") and sidewall angle ("SWA"). For some profile types, two parameters may be adequate, such as the quartic profile type of FIG. 4B, which may be characterized by the coefficient a and height of the profile. As noted above, the set of initial parameter values of the profile type selected is such that the predicted profile using the profile type from the gallery is the closest match to the simulated profile. Thus, as noted above in reference to FIG. 5B, a spectrum or spectra of a radiation parameter over a range of wavelengths 116 is arrived at using the diffraction solver 108 which corresponds to the set of initial values 252 of the profile type selected and its associated films. This spectrum or spectra are then compared with the measured data as in block 122 of FIG. 5A and a non-linear optimization tool may be utilized as described to arrive after convergence, along path 254, at a final set 260 of parameter values of the profile type. If the profile type of FIG. 4A is selected, for example, the final set 260 would comprise the final values of the CD, height and sidewall angle of each trapezoid.

In order to speed up the process described in reference to FIG. 5A, a coarse library such as that indicated in FIG. 6B may be pre-computed off-line, so that each profile type in the gallery is stored together with a number of sets of initial parameter values, such as those corresponding to the intersection points (e.g., 252) in the grid-like structure in FIG. 6B, and their corresponding spectra. The diffraction solver 108 is then used to compute the spectrum corresponding to each of the intersection points and such spectra are stored together with the profile type and the associated sets of initial parameter values at the intersection points. Then, when a simulated profile becomes available, such as simulated profile 244 in FIG. 6A, such simulated profile is then matched against the predicted profiles that correspond to the different sets of initial parameter values corresponding to the intersection points in FIG. 6B in the coarse library. From this comparison, a particular intersection point in the grid-like structure and the corresponding set of initial parameter values may be quickly identified and the process of blocks 120, 122, 124 and 126 of FIG. 5A may be carried out very quickly to locate the final set 260 of parameter values of the profile type. Thus, while the resolution of the coarse library of FIG. 6B is not sufficient for measurement, it provides significant acceleration of non-linear optimization. Where a coarse library is not constructed before hand, the center point 250, its corresponding set of parameter values and spectra, may be used as the starting point for the optimization process in FIG. 5A.

The above-described radiation parameters may be measured in a manner known to those in the art, using the systems in FIGS. 1A and 2. Another aspect of the invention is based on the observation that certain radiation parameters may be more sensitive to the change in one or more parameters associated with the profile type and related films than other radiation parameters. This is illustrated in FIG. 6C. From the profile type, its associated film(s) and the initial values 252 of the parameters selected, the diffraction solver 108 generates predicted spectra of different radiation parameters. Shown as examples in FIG. 6C are the spectra 270 for four different radiation parameters that are so generated: $R_S$, $R_P$, $\cos\Delta$ and $\tan\psi$. The different parameter values (e.g. CD, H, SWA) associated with the profile type are then varied and the diffraction solver 108 is used to generate a set of different spectra for each of the four or more different radiation parameters. By comparing the change in spectra of the four or more radiation parameters corresponding to the same variation in parameter value (e.g. CD, H, SWA), the radiation parameter and its corresponding spectra that is the most sensitive to the change in parameter value is then identified.

In other words, each of the selected profile types is varied. Thus, if the profile type of FIG. 4A is selected, then each of the parameters CD, H and SWA is varied. For each variation of each of the three parameters, diffraction solver 108 computes the corresponding spectrum for each of the four or more radiation parameters. A quantity $x^2$ may be defined by the equation:

$$\chi^2 = \frac{1}{N}\sum_{n=1}^{N} \frac{[R_1(\lambda_n) - R_2(\lambda_n)]^2}{\sigma_n^2}$$

This quantity ($x^2$) measures the difference between two sets of data $R_1$ and $R_2$, which can be, e.g., the theoretical and the experimental values of a certain signal ($R_S$,$R_P$,$\cos\Delta$, . . . ). The values $\sigma_n$ set the weight of the n-th data point and are typically defined by the experimental uncertainty. In calculating $x^2$ in FIG. 6C, actually two theoretical spectra are compared—one at the initial parameter values with the one at a modified parameter values. Quantities other than $x^2$ may also be used in optimization—for example, the cross-correlation between the compared spectra may be optimized.

The quantity $x^2$, along path 254, is thus computed according to the equation above, which is the difference between two theoretical spectra—one at the initial parameter values 252 and the one where one of the parameter values has been modified from its initial value. In the four sets of spectra 270 shown in FIG. 6C, a number of curves are computed for each of the four radiation parameters, where each curve corresponds to the theoretical spectrum with one of the parameters having a value that is modified compared to the initial value. The four quantities $X^2$ of the four radiation parameters corresponding to the same modification in CD, H or SWA are then compared to identify the radiation parameter that is the most sensitive to a change in CD, H or SWA, and its spectra. In the example 274 shown in FIG. 6C, $x^2$ is the largest for the radiation parameter $\tan\psi$. Therefore, if the radiation parameter $\tan\psi$ is chosen for the modeling process shown in FIG. 5A, a more accurate result may be achievable. In other words, when the apparatus of FIG. 1A or 2 is used to measure the spectra associated with the diffracting structure and any associated films (block 120 in FIG. 5A), the radiation parameter $\tan\psi$ is measured over a range of wavelengths, and such spectrum is then compared (block 122) to $\tan\psi$ generated by the diffraction solver 108 in the flowchart of FIG. 5A, to arrive at a more accurate set of values for the final set 260 of FIG. 6B.

FIG. 6C illustrates four of the radiation parameters that may be used. A more complete list includes the following 12 radiation parameters:

$$R_s, R_p, R_s - R_p, \cos\Delta, \tan\psi = |r_p/r_s|,$$

$$R_s/R_p, X = |r_s - r_p|^2, Y = |r_s + r_p|^2, X/Y, (X-Y)/(X+Y)$$

$$\alpha = \frac{R_p\cos^2 A - R_s\sin^2 A}{R_p\cos^2 A + R_s\sin^2 A},$$

$$\beta = \frac{2\sqrt{R_p\cos^2 A}\sqrt{R_s\sin^2 A}}{R_p\cos^2 A + R_s\sin^2 A}\cos\Delta$$

where $r_S$ and $r_P$ denote the complex amplitude reflection coefficients for S and P polarizations respectively, while $R_S$ and $R_P$ are the reflectivities for S and P polarizations respectively: $R_S=|r_S|^2, R_P=|r_P|^2$. The angle A is the analyzer angle and can be (optimally) set by hardware configuration. The quantities $\tan\psi$ and $\cos\Delta$ are ellipsometric parameters known to those in the art.

It will be noted that the process described in reference to FIGS. 5A, 5B takes into account both profile and film parameters, so that the process described above in reference to FIG. 6C selects the radiation parameter and its associated spectra that is the most sensitive to a variation in a profile and/or film parameter.

The advantages provided by different aspects of the process described above are set forth in the table below.

| FIGS. 6A, 6B, 6C. Off-line techniques developed and used in this invention that allow real-time measurement of profile and film stack parameters by the method of FIGS. 5A, 5B ||
| --- | --- |
| Method | Advantage |
| Analysis of manufacturing process information by a lithography simulation tool (FIG. 6A). | Optimal choice of profile model and process window for parameters |
| Selection of one or more signals (spectra) that are most sensitive to parameters of interest (FIG. 6C) | Ability to measure both profile and film parameters by selecting most sensitive signals |
| Generation of a look-up table of eigenvalues in the grating | Replacement of the eigenvalue computation by interpolation to |

-continued

| Method | Advantage |
| --- | --- |
| FIGS. 6A, 6B, 6C. Off-line techniques developed and used in this invention that allow real-time measurement of profile and film stack parameters by the method of FIGS. 5A, 5B | |
| region | speed up the diffraction solver in the real-time measurement |
| Generation of a coarse library of spectra within the process window (FIG. 6B) | Best initial seed to accelerate the convergence of nonlinear optimization |

FIG. 7 is a block diagram of an integrated spectroscopic diffraction-based metrology system, a photolithographic track/stepper and an etcher to illustrate another aspect of the invention. A layer of material such as photoresist is formed on the surface of a semiconductor wafer by means of track/stepper 350, where the photoresist forms a grating structure on the wafer. One or more of the CD, H, SWA and/or other parameters of the grating structure are then measured using systems 10, 80 of FIGS. 1A, 2 and one or more of the above-described techniques may be employed if desired to find the value(s) of the one or more parameters of the photoresist pattern and its associated film(s). Such value (s) from the computer 40 are then fed back to the track/stepper 350, where such information may be used to alter the lithographic process in track/stepper 350 to correct any errors. In semiconductor processing, after a layer of photoresist has been formed on the wafer, an etching process may be performed, such as by means of etcher 360. The layer of photoresist is then removed in a manner known in the art and the resulting grating structure made of semiconductor material on the wafer may again be measured if desired using system 10 or 80. The value(s) measured using any one or more of the above-described techniques may be supplied to the etcher for altering any one of the etching parameters in order to correct any errors that have been found using system 10 or 80. Of course, the results obtained by one or more of the above described techniques in system 10, 80 may be used in both the track/stepper and the etcher, or in either the track/stepper or the etcher but not both. The track/stepper 350 and/or etcher 360 may form an integrated single tool with the system 10 or 80 for finding the one or more parameters of a diffracting structure, or may be separate instruments from it.

FIG. 8 is a schematic view of the track/stepper 350 and an associated flowchart illustrating a process for semiconductor wafer processing to illustrate in more detail the points of integration of the processing process with the detection of profiles of diffracting structures and associated films to illustrate in more detail a part of the process in FIG. 7. As shown in FIG. 8, a semiconductor wafer 352 may be loaded from a cassette loader 354 to several stations labeled "prime," "coat," "soft bake," "EBR." Then the wafer 352 is delivered by a stepper interface 356 to exposure tool 358. The different processes at the four locations mentioned above are set forth below:

At the location "Prime", the wafer undergoes chemical treatment before a layer of photoresist is spun on it, so that the photoresist layer can stick to wafer. At the location "Coat", a layer of photoresist coating is spun onto the wafer. At "Soft bake", the layer of resist is baked to remove chemical solvent from the resist. At "EBR" which stands for "edge-bead removal", a solvent nozzle or laser is used to remove excess photoresist from the edge of wafer.

After the wafer has been exposed to radiation by tool 358, the wafer then undergoes four additional processes: "PEB," "PEB chill," "Develop," and "Hard bake." At "PEB or post exposure bake", the wafer is baked to reduce standing-wave effect from the exposure tool. Then it is cooled at "PEB chill". The wafer is then washed with reagent to develop the photoresist, so that unexposed (negative) or exposed (positive) photoresist is removed. The wafer then is baked at "Hard bake" to stabilize the photoresist pattern. It will be noted that all of the components of device 350 of FIG. 8 except for the "exposure tool" 358 is known as the "Track" (also called cluster).

After these latter four processes have been completed, the wafer 352 is then returned to the cassette loader 354 and this completes the processing involving the stepper 350. The detection system 10 or 80 may be applied at arrow 362 to measure the parameters of the diffracting structure and associated film(s). Thus, such parameters may be measured after "hard bake."

Software Upgrades

The invention has been described above, employing a system such as that shown in FIGS. 1A and 2. While the various optical components in the system of FIGS. 1A and 2 are used to obtain measured data from the sample, many of the other processes are performed by computer 40 (not shown in FIG. 2 to simplify the figure). Thus, for many systems currently being used by manufacturers such as semiconductor manufacturers, the computers used in the systems may not have the capability to perform the techniques described above. Thus, another aspect of the invention envisions that the software in these computers can be upgraded so that computer 40 can perform one or more of the above described different functions. Therefore, another aspect of the invention involves the software components that are loaded to computer 40 to perform the above-described functions. These functions, in conjunction with the optical components of system 10 or 80 in FIG. 1A or 2, provide results with the different advantages outlined above. The software or program components may be installed in computer 40 in a variety of ways.

As will be understood in the art, the inventive software components may be embodied in a fixed media program component containing logic instructions and/or data that when loaded into an appropriately configured computing device to cause that device to perform according to the invention. As will be understood in the art, a fixed media program may be delivered to a user on a fixed media for loading in a users computer or a fixed media program can reside on a remote server that a user accesses through a communication medium in order to download a program component. Thus another aspect of the invention involves transmitting, or causing to be transmitted, the program component to a user where the component, when downloaded into the user's device, can perform any one or more of the functions described above.

FIG. 9 shows an information appliance (or digital device) that may be understood as a logical apparatus that can read instructions from media 417 and/or network port 419. Apparatus 40 can thereafter use those instructions to direct server or client logic, as understood in the art, to embody aspects of the invention. One type of logical apparatus that may embody the invention is a computer system as illustrated in 40, containing CPU 404, optional input devices 409 and 411, disk drives 415 and optional monitor 405. Fixed media 417 may be used to program such a system and may represent a disk-type optical or magnetic media, magnetic tape, solid state memory, etc. One or more aspects of the invention may be embodied in whole or in part as software recorded on this fixed media. Communication port 419 may also be used to initially receive instructions that are used to program such a system to perform any one or more of the above-described functions and may represent any type of communication connection, such as to the internet or any other computer network. The instructions or program may be transmitted directly to a user's device or be placed on a network, such as a website of the internet to be accessible through a user's device. All such methods of making the program or software component available to users are known to those in the art and will not be described here.

The invention also may be embodied in whole or in part within the circuitry of an application specific integrated circuit (ASIC) or a programmable logic device (PLD). In such a case, the invention may be embodied in a computer understandable descriptor language which may be used to create an ASIC or PLD that operates as herein described.

While the invention has been described above by reference to various embodiments, it will be understood that changes and modifications may be made without departing from the scope of the invention, which is to be defined only by the appended claims and their equivalents. All references referred to herein are incorporated by reference in their entireties.

What is claimed is:

1. A method for finding a profile of a structure on and/or below one or more layers of material, said structure having a dimension in the micron or sub-micron range and fabricated by a process, wherein a measurement is carried out by directing a polychromatic beam of electromagnetic radiation at said structure and detecting at a number of wavelengths corresponding radiation data from said beam after it has been modified by the structure and the one or more layers, comprising:

providing a gallery of profile types, each profile type and the one or more layers associated with a set of one or more parameters and a set of radiation data at the number of wavelengths;

selecting a profile type from the gallery based on information on the process;

carrying out a measurement of the structure to obtain measured radiation data from said beam after it has been modified by the structure and the one or more layers; and comparing the measured radiation data to the set of radiation data associated with the selected profile type to arrive at a set of value(s) of the one or more parameters.

2. The method of claim 1, wherein said providing provides a gallery where at least one of the profile types is defined using a polynomial function.

3. The method of claim 2, wherein said providing provides a gallery where at least one of the profile types is defined using a quartic parabola or a combination of quartic and quadratic parabolas.

4. The method of claim 1, wherein said at least one profile type comprises a periodic structure having a plurality of layers of material with different optical properties.

5. The method of claim 1, wherein said selecting includes simulating a profile using information concerning a fabrication process, and comparing the simulated profile to the gallery to select a profile type in the gallery that is a match to the simulated profile.

6. The method of claim 5, wherein said selecting further includes selecting an initial set of values of the one or more parameters of the selected profile type based on the comparison between the simulated profile and the selected profile type.

7. The method of claim 6, further comprising generating a set of radiation data associated with the selected profile type using the initial set of values.

8. The method of claim 1, wherein at least one of said profile types has bottom footers.

9. The method of claim 1, wherein said providing provides a gallery where at least one profile type in the gallery includes one or more slabs defined by an analytical function.

10. The method of claim 9, wherein said providing provides a gallery where at least one profile type in the gallery includes one or more rectangular or trapezoidal slabs.

11. The method of claim 1, wherein at least one of said profile types has one or more sidewall spacers or a three-dimensional structure.

12. The method of claim 11, wherein said sidewall spacers are composed of a material different from that of the slab(s).

13. The method of claim 1, wherein said providing provides a gallery where at least one of the profile types is defined by means of a multi-slab model.

14. The method of claim 1, wherein said one or more parameters include one or more of the following: width, height and sidewall angle, thickness and index of refraction.

15. The method of claim 1, wherein said comparing includes applying a non-linear optimization process.

16. The method of claim 1, wherein said profile types provided are associated with a set of radiation data related to reflectance, transmittance or ellipsometric parameters of the profile type.

17. The method of claim 1, wherein at least one of said profile types provided is associated with a plurality of sets of radiation data of different radiation parameters, said radiation parameters including reflectance or transmittance parameters and ellipsometric parameters of the profile type, said method further comprising selecting at least one radiation parameter and at least one set of radiation data based on sensitivity of such data to a change in the one or more parameters of the profile type and/or of the one or more layers.

18. The method of claim 1, wherein the comparing arrives at a set of value(s) of the one or more parameters of the selected profile type and/or of the one or more layers.

19. A method for finding a profile of a structure on and/or below one or more layers of material, said structure having a dimension in the micron or sub-micron range and fabricated by a process, wherein a measurement is carried out by directing a polychromatic beam of electromagnetic radiation at said structure and detecting at a number of wavelengths corresponding radiation data from said beam after it has been modified by the structure, comprising:

providing a gallery of a plurality of profile types, each profile type and the one or more layers associated with a set of one or more parameters and a set of radiation data at the number of wavelengths, wherein at least one of said profile types provided is associated with a plurality of sets of radiation data of different radiation parameters, said different radiation parameters including reflectance or transmittance parameters, and ellipsometric parameters of the profile type;

selecting a profile type from the gallery, at least one radiation parameter and at least one set of radiation data associated with such profile type based on sensitivity of such data to a change in the one or more parameters of the profile type and/or of the one or more layers;

carrying out a measurement of the structure to obtain measured radiation data from said beam after it has been modified by the structure at the number of wavelengths; and comparing the measured radiation data to the at least one set of radiation data associated with the selected profile type to arrive at a set of value(s) of the one or more parameters.

20. The method of claim 19, wherein said selecting selects a radiation parameter and one or more sets of radiation data based on sensitivity of such data to a change in the profile parameters associated with the profile type and/or with the one or more layers.

21. The method of claim 19, wherein said providing provides a gallery where at least one of the profile types is defined using a polynomial function.

22. The method of claim 21, wherein said providing provides a gallery where at least one of the profile types is defined using a quartic parabola or a combination of quartic and quadratic parabolas.

23. The method of claim 19, wherein said at least one profile type comprises a periodic structure having a plurality of layers of material with different optical properties.

24. The method of claim 19, wherein said selecting includes simulating a profile using information concerning a fabrication process, and comparing the simulated profile to the gallery to select a profile type in the gallery that is a match to the simulated profile.

25. The method of claim 24, wherein said selecting further includes selecting an initial set of values of the one or more parameters of the selected profile type based on the comparison between the simulated profile and the selected profile type.

26. The method of claim 25, further comprising generating a set of radiation data associated with the selected profile type using the initial set of values.

27. The method of claim 19, wherein at least one of said profile types has bottom footers.

28. The method of claim 19, wherein said providing provides a gallery where at least one profile type in the gallery includes one or more slabs defined by an analytical function.

29. The method of claim 28, said providing provides a gallery where at least one profile type in the gallery includes one or more rectangular or trapezoidal slabs.

30. The method of claim 19, wherein at least one of said profile types has one or more sidewall spacers or a three-dimensional structure.

31. The method of claim 30, wherein said sidewall spacers are composed of a material different from that of the slab(s).

32. The method of claim 19, wherein said providing provides a gallery where at least one of the profile types is defined by means of a multi-slab model.

33. The method of claim 19, wherein said one or more parameters include one or more of the following: width, height and sidewall angle, thickness and index of refraction.

34. The method of claim 19, wherein said comparing includes applying non-linear optimization.

35. The method of claim 19, wherein said profile types provided are associated with a set of radiation data related to reflectance, transmittance or ellipsometric parameters of the profile type.

36. The method of claim 19, wherein the comparing arrives at a set of value(s) of the one or more parameters of the selected profile type and/or of the one or more layers.

37. A computer readable storage device embodying a program of instructions executable by a computer to perform a method for finding a profile of a structure on and/or below one or more layers of material, said structure having a dimension in the micron or sub-micron range and fabricated by a process, wherein a measurement is carried out by directing a polychromatic beam of electromagnetic radiation at said structure, detecting at a number of wavelengths corresponding radiation data from said beam after it has been modified by the structure and the one or more layers at a number of wavelengths to provide measured radiation data; said method comprising:

providing a gallery of a plurality of profile types, each profile type and the one or more layers associated with a set of one or more parameters and a set of radiation data at the number of wavelengths;

selecting a profile type from the gallery based on information on the process; and comparing the measured radiation data to the set of radiation data associated with the selected profile type to arrive at a set of value(s) of the one or more parameters of the selected profile type and/or of the one or more layers.

38. The device of claim 37, wherein said providing provides a gallery where at least one of the profile types is defined using a quartic parabola or a combination of quartic and quadratic parabolas.

39. The device of claim 37, wherein said at least one profile type comprises a periodic structure having a plurality of layers of material with different optical properties.

40. The device of claim 37, wherein said selecting includes simulating a profile using information concerning a fabrication process, and comparing the simulated profile to the gallery to select a profile type in the gallery that is a match to the simulated profile.

41. The device of claim 40, wherein said selecting further includes selecting an initial set of values of the one or more parameters of the selected profile type based on the comparison between the simulated profile and the selected profile type.

42. The device of claim 41, further comprising generating a set of radiation data associated with the selected profile type using the initial set of values.

43. The device of claim 37, wherein at least one of said profile types has bottom footers.

44. The device of claim 37, said providing provides a gallery where at least one profile type in the gallery includes one or more slabs defined by an analytical function.

45. The device of claim 44, said providing provides a gallery where at least one profile type in the gallery includes one or more rectangular or trapezoidal slabs.

46. The device of claim 37, wherein at least one of said profile types has one or more sidewall spacers or a three-dimensional structure.

47. The device of claim 46, wherein said sidewall spacers are composed of a material different from that of the slab(s).

48. The device of claim 37, wherein said profile types provided are associated with a set of radiation data related to reflectance, transmittance or ellipsometric parameters of the profile type.

49. The device of claim 37, wherein at least one of said profile types provided is associated with a plurality of sets of radiation data of different radiation parameters, said radiation parameters including reflectance or transmittance parameters and ellipsometric parameters of the profile type, said method further comprising selecting at least one radiation parameter and at least one set of radiation data based on sensitivity of such data to a change in the one or more parameters of the profile type and/or of the one or more layers.

50. A computer readable storage device embodying a program of instructions executable by a computer to perform a method for finding a profile of a structure on and/or below one or more layers of material, said structure having a dimension in the micron or sub-micron range and fabricated by a process, wherein the system measures the structure by directing a polychromatic beam of electromagnetic radiation at said structure, detecting corresponding radiation data from said beam after it has been modified by the structure and the one or more layers at a number of wavelengths to provide measured radiation data; said method comprising:

provided a gallery of a plurality of profile types, each profile type and the one or more layers associated with a set of one or more parameters and a set of radiation data at the number of wavelengths, wherein at least one of said profile types provided is associated with a plurality of sets of radiation data of different radiation parameters, said different radiation parameters including reflectance or transmittance parameters and ellipsometric parameters;

selecting a profile type from the gallery, at least one radiation parameter and at least one set of radiation data based on sensitivity of such data to a change in the one or more parameters of the profile type and/or of the one or more layers; and comparing the measured radiation data to the at least one set of radiation data associated with the selected profile type to arrive at a set of value(s) of the one or more parameters of the selected profile type.

51. The device of claim 50, wherein said providing provides a gallery where at least one of the profile types is defined using a quartic parabola or a combination of quartic and quadratic parabolas.

52. The device of claim 51, wherein said profile types provided are associated with a set of radiation data related to reflectance, transmittance or ellipsometric parameters of the profile type.

53. The device of claim 51, wherein at least one of said profile types provided is associated with a plurality of sets of radiation data of different radiation parameters, said radiation parameters including reflectance or transmittance parameters and ellipsometric parameters of the profile type, said method further comprising selecting at least one radiation parameter and at least one set of radiation data based on sensitivity of such data to a change in the one or more parameters of the profile type and/or of the one or more layers.

54. The device of claim 50, wherein said at least one profile type comprises a periodic structure having a plurality of layers of material with different optical properties.

55. The device of claim 50, wherein said selecting includes simulating a profile using information concerning a fabrication process, and comparing the simulated profile to the gallery to select a profile type in the gallery that is a match to the simulated profile.

56. The device of claim 55, wherein said selecting further includes selecting an initial set of values of the one or more parameters of the selected profile type based on the comparison between the simulated profile and the selected profile type.

57. The device of claim 56, further comprising generating a set of radiation data associated with the selected profile type using the initial set of values.

58. The device of claim 50, wherein at least one of said profile types has bottom footers.

59. The device of claim 50, wherein said providing provides a gallery where at least one profile type in the gallery includes one or more slabs defined by an analytical function.

60. The device of claim 59, wherein said providing provides a gallery where at least one profile type in the gallery includes one or more rectangular or trapezoidal slabs.

61. The device of claim 50, wherein at least one of said profile types has one or more sidewall spacers or a three-dimensional structure.

62. The device of claim 61, wherein said sidewall spacers are composed of a material different from that of the slab(s).

63. A method for transmitting a program of instructions executable by a computer to perform a method for finding a profile of a structure on and/or below one or more layers of material, said structure having a dimension in the micron or sub-micron range and fabricated by a process, wherein a measurement is carried out by directing a polychromatic beam of electromagnetic radiation at said structure, detecting corresponding radiation data from said beam after it has been modified by the structure and the one or more layers at a number of wavelengths to provide measured radiation data; said method comprising:

causing a program of instructions to be transmitted to a client device, thereby enabling the client device to perform, by means of such program, the following process:

providing a gallery of profile types, each profile type and the one or more layers associated with a set of one or more parameters and a set of radiation data at the number of wavelengths;

selecting a profile type from the gallery based on information on the process; and comparing the measured radiation data to the set of radiation data associated with the selected profile type to arrive at a set of value(s) of the one or more parameters of the selected profile type to arrive at a set of value(s) of the one or more parameters.

64. The method of claim 63, wherein said providing provides a gallery where at least one of the profile types is defined using a quartic parabola or a combination of quartic and quadratic parabolas.

65. The method of claim 63, wherein said at least one profile type comprises a periodic structure having a plurality of layers of material with different optical properties.

66. The method of claim 63, wherein said selecting includes simulating a profile using information concerning a fabrication process, and comparing the simulated profile to the gallery to select a profile type in the gallery that is a match to the simulated profile.

67. The method of claim 66, wherein said selecting further includes selecting an initial set of values of the one or more parameters of the selected profile type based on the comparison between the simulated profile and the selected profile type.

68. The method of claim 67, further comprising generating a set of radiation data associated with the selected profile type using the initial set of values.

69. The method of claim 63, wherein at least one of said profile types has bottom footers.

70. The method of claim 63, wherein said providing provides a gallery where at least one profile type in the gallery includes one or more slabs defined by an analytical function.

71. The method of claim 70, said providing provides a gallery where at least one profile type in the gallery includes one or more rectangular or trapezoidal slabs.

72. The method of claim 63, wherein at least one of said profile types has one or more sidewall spacers or a three-dimensional structure.

73. The method of claim 72, wherein said sidewall spacers are composed of a material different from that of the slab(s).

74. The method of claim 63, wherein said profile types provided are associated with a set of radiation data related to reflectance, transmittance or ellipsometric parameters of the profile type.

75. The method of claim 63, wherein at least one of said profile types provided is associated with a plurality of sets of radiation data of different radiation parameters, said radiation parameters including reflectance or transmittance parameters and ellipsometric parameters of the profile type, said process further comprising selecting at least one radiation parameter and at least one set of radiation data based on sensitivity of such data to a change in the one or more parameters of the profile type and/or of the one or more layers.

76. A method for transmitting a program of instructions executable by a computer to perform a method for finding a profile of a structure on and/or below one or more layers of material, said structure having a dimension in the micron or sub-micron range and fabricated by a process, wherein the system measures the structure by directing a polychromatic beam of electromagnetic radiation at said structure, detecting corresponding radiation data from said beam after it has been modified by the structure and the one or more layers at a number of wavelengths to provide measured radiation data; said method comprising:

causing a program of instructions to be transmitted to a client device, thereby enabling the client device to perform, by means of such program, the following process:

providing a gallery of profile types, each profile type and the one or more layers associated with a set of one or more parameters and a set of radiation data at the number of wavelengths, wherein at least one of said profile types provided is associated with a plurality of sets of radiation data of different radiation parameters, said different radiation parameters including reflectance or transmittance parameters and ellipsometric parameters;

selecting a profile type from the gallery, at least one radiation parameter and at least one set of radiation data based on sensitivity of such data to a change in the one or more parameters of the profile type and/or of the one or more layers; and comparing the measured radiation data to the at least one set of radiation data to arrive at a set of value(s) of the one or more parameters.

77. The method of claim 76, wherein said providing provides a gallery where at least one of the profile types is defined using a quartic parabola or a combination of quartic and quadratic parabolas.

78. The method of claim 76, wherein said at least one profile type comprises a periodic structure having a plurality of layers of material with different optical properties.

79. The method of claim 76, wherein said selecting includes simulating a profile using information concerning a fabrication process, and comparing the simulated profile to the gallery to select a profile type in the gallery that is a match to the simulated profile.

80. The method of claim 79, wherein said selecting further includes selecting an initial set of values of the one or more parameters of the selected profile type based on the comparison between the simulated profile and the selected profile type.

81. The method of claim 80, further comprising generating a set of radiation data associated with the selected profile type using the initial set of values.

82. The method of claim 76, wherein at least one of said profile types has bottom footers.

83. The method of claim 76, wherein said providing provides a gallery where at least one profile type in the gallery includes one or more slabs defined by an analytical function.

84. The method of claim 83, said providing provides a gallery where at least one profile type in the gallery includes one or more rectangular or trapezoidal slabs.

85. The method of claim 76, wherein at least one of said profile types has one or more sidewall spacers or a three-dimensional structure.

86. The method of claim 85, wherein said sidewall spacers are composed of a material different from that of the slab(s).

87. A method for finding a profile of a structure having a dimension in the micron or sub-micron range and fabricated by a process, wherein a measurement is carried out by directing a polychromatic beam of electromagnetic radiation at said structure and detecting at a number of wavelengths corresponding radiation data from said beam after it has been modified by the structure, comprising:

providing a gallery of profile types, each profile type associated with a set of one or more parameters and a set of radiation data at the number of wavelengths;

selecting a profile type from the gallery based on information on the process;

carrying out a measurement of the structure to obtain measured radiation data from said beam after it has been modified by the structure; and comparing the measured radiation data to the set of radiation data associated with the selected profile type to arrive at a set of value(s) of the one or more parameters of the selected profile type.

88. A method for finding a profile of a structure, said structure having a dimension in the micron or sub-micron range and fabricated by a process, wherein a measurement is carried out by directing a polychromatic beam of electromagnetic radiation at said structure and detecting at a number of wavelengths corresponding radiation data from said beam after it has been modified by the structure, comprising:

providing a gallery of a plurality of profile types, each profile type associated with a set of one or more parameters and a set of radiation data at the number of wavelengths of different radiation parameters, wherein at least one of said profile types provided is associated with a plurality of sets of different radiation data, said different radiation parameters including reflectance or transmittance parameters, and ellipsometric parameters of the profile type;

selecting a profile type from the gallery, at least one radiation parameter and at least one set of radiation data associated with such profile type based on sensitivity of such data to a change in the one or more parameters;

carrying out a measurement of the structure to obtain measured radiation data from said beam after it has been modified by the structure at the number of wavelengths; and comparing the measured radiation data to the at least one set of radiation data associated with the selected profile type to arrive at a set of value(s) of the one or more parameters of the selected profile type.

89. A computer readable storage device embodying a program of instructions executable by a computer to perform a method for finding a profile of a structure, said structure having a dimension in the micron or sub-micron range and fabricated by a process, wherein a measurement is carried out by directing a polychromatic beam of electromagnetic radiation at said structure, detecting at a number of wavelengths corresponding radiation data from said beam after it has been modified by the structure at a number of wavelengths to provide measured radiation data; said method comprising:

providing a gallery of a plurality of profile types, each profile associated with a set of one or more parameters and a set of radiation data at the number of wavelengths;

selecting a profile type from the gallery based on information on the process; and comparing the measured radiation data to the set of radiation data associated with the selected profile type to arrive at a set of value(s) of the one or more parameters of the selected profile type.

90. A computer readable storage device embodying a program of instructions executable by a computer to perform a method for finding a profile of a structure having a dimension in the micron or sub-micron range and fabricated by a process, wherein the system measures the structure by directing a polychromatic beam of electromagnetic radiation at said structure, detecting corresponding radiation data from said beam after it has been modified by the structure at a number of wavelengths to provide measured radiation data; said method comprising:

providing a gallery of a plurality of profile types, each profile associated with a set of one or more parameters and a set of radiation data at the number of wavelengths, wherein at least one of said profile types provided is associated with a plurality of sets of radiation data of different radiation parameters, said different radiation parameters including reflectance or transmittance parameters and ellipsometric parameters;

selecting a profile type from the gallery, at least one radiation parameter and at least one set of radiation data based on sensitivity of such data to a change in the one or more parameters; and comparing the measured radiation data to the at least one set of radiation data associated with the selected profile type to arrive at a set of value(s) of the one or more parameters of the selected profile type.

91. A method for transmitting a program of instructions executable by a computer to perform a method for finding a profile of a structure having a dimension in the micron or sub-micron range and fabricated by a process, wherein the system measures the structure by directing a polychromatic beam of electromagnetic radiation at said structure, detecting corresponding radiation data from said beam after it has been modified by the structure at a number of wavelengths to provide measured radiation data; said method comprising:

causing a program of instructions to be transmitted to a client device, thereby enabling the client device to perform, by means of such program, the following process:

providing a gallery of profile types, each profile type associated with a set of one or more parameters and a set of radiation data at the number of wavelengths;

selecting a profile type from the gallery based on information on the process; and comparing the measured radiation data to the set of radiation data associated with the selected profile type to arrive at a set of value(s) of the one or more parameters of the selected profile type to arrive at a set of value(s) of the one or more parameters.

92. A method for transmitting a program of instructions executable by a computer to perform a method for finding a profile of a structure having a dimension in the micron or sub-micron range and fabricated by a process, wherein measurement is carried out by directing a polychromatic beam of electromagnetic radiation at said structure, detecting corresponding radiation data from said beam after it has been modified by the structure at a number of wavelengths to provide measured radiation data; said method comprising:

causing a program of instructions to be transmitted to a client device, thereby enabling the client device to perform, by means of such program, the following process:

providing a gallery of profile types, each profile type associated with a set of one or more parameters and a set of radiation data at the number of wavelengths, wherein at least one of said profile types provided is associated with a plurality of sets of radiation data of different radiation parameters, said different radiation parameters including reflectance or transmittance parameters and ellipsometric parameters;

selecting a profile type from the gallery, at least one radiation parameter and at least one set of radiation data based on sensitivity of such data to a change in the one or more parameters; and comparing the measured radiation data to the at least one set of radiation data to arrive at a set of value(s) of the one or more parameters.

* * * * *